(12) United States Patent
Wang et al.

(10) Patent No.: US 9,824,287 B2
(45) Date of Patent: Nov. 21, 2017

(54) METHOD, APPARATUS AND SYSTEM FOR BIOMETRIC IDENTIFICATION

(71) Applicant: HUAMI INC., Mountain View, CA (US)

(72) Inventors: Fei Wang, Mountain View, CA (US); Ting Chen, Mountain View, CA (US)

(73) Assignee: Huami Inc., Mountain View, CA (US)

( * ) Notice: Subject to any disclaimer, the term of this patent is extended or adjusted under 35 U.S.C. 154(b) by 207 days.

(21) Appl. No.: 15/047,140

(22) Filed: Feb. 18, 2016

(65) Prior Publication Data

US 2017/0091567 A1    Mar. 30, 2017

Related U.S. Application Data

(63) Continuation-in-part of application No. 14/869,088, filed on Sep. 29, 2015.

(51) Int. Cl.
*G06K 9/00* (2006.01)
*G06N 99/00* (2010.01)
(Continued)

(52) U.S. Cl.
CPC ...... *G06K 9/00892* (2013.01); *A61B 5/02028* (2013.01); *A61B 5/04012* (2013.01);
(Continued)

(58) Field of Classification Search
CPC ...... G06F 21/32; G06F 21/34; G06F 19/3418; G06F 21/35; G06F 21/31; G06F 21/445;
(Continued)

(56) References Cited

U.S. PATENT DOCUMENTS 4,809,705 A    3/1989  Ascher
6,970,737 B1   11/2005 Brodnick et al.
(Continued)

FOREIGN PATENT DOCUMENTS

CN    103284702 A    9/2013
CN    103598877      2/2014
(Continued)

OTHER PUBLICATIONS

Tantawi, M.; Salem, A.; Tolba, M. F.:Fiducial Based Approach to ECG Biometrics Using Limited Fiducial Points. In: Advanced Machine Learning Technologies and Applications Communications in Computer and Information Science, vol. 488, pp. 199-210 (2014).
(Continued)

*Primary Examiner* — Mark Blouin
(74) *Attorney, Agent, or Firm* — Young Basile Hanlon & MacFarlane, P.C.

(57) ABSTRACT

Method and apparatus for processing a biometric measurement signal using a computing device, including receiving biometric measurement records associated with a first biometric measurement generated by contact with a single individual, extracting, for each of the biometric measurement records, feature data including periodic features extracted from the biometric measurement records, determining, pairing data comprising candidate pairs between the feature data and defined profiles associated with a known individual, wherein a candidate pair is associated with one of the periodic features and one of the defined profiles associated with the known individual, determining, for the candidate pair, a similarity value based on the one of the periodic features and the one of the defined profiles associated with the known individual, and determining whether a match exists between the single individual and the known
(Continued)

individual based on a combination of the similarity values determined for the candidate pairs.

20 Claims, 7 Drawing Sheets

(51) Int. Cl.
*G06K 9/46* (2006.01)
*G06K 9/62* (2006.01)
*A61B 5/0452* (2006.01)
*A61B 5/02* (2006.01)
*A61B 5/04* (2006.01)

(52) U.S. Cl.
CPC .......... *A61B 5/0452* (2013.01); *G06K 9/4604* (2013.01); *G06K 9/6215* (2013.01); *G06N 99/005* (2013.01); *G06K 2009/00939* (2013.01)

(58) Field of Classification Search
CPC . G06F 21/6245; G06F 19/322; G06F 19/3406
USPC ........................................................ 340/5.82
See application file for complete search history.

(56) References Cited

U.S. PATENT DOCUMENTS

| | | | |
|---|---|---|---|
| 7,171,269 B1 | 1/2007 | Addison et al. | |
| 7,630,521 B2* | 12/2009 | Kim ................... | G06K 9/00496 382/115 |
| 8,049,597 B1* | 11/2011 | Murakami ............. | G06F 21/32 340/5.1 |
| 8,762,733 B2 | 6/2014 | Derchak et al. | |
| 8,994,498 B2* | 3/2015 | Agrafioti ................ | G06F 21/40 340/5.52 |
| 2007/0253624 A1 | 11/2007 | Becker | |
| 2010/0090798 A1 | 4/2010 | Garcia Molina et al. | |
| 2011/0254662 A1 | 10/2011 | Lindsay | |
| 2014/0120876 A1 | 5/2014 | Shen | |
| 2014/0188770 A1 | 7/2014 | Agrafioti et al. | |
| 2014/0361871 A1 | 12/2014 | Silva et al. | |
| 2015/0199010 A1 | 7/2015 | Coleman et al. | |
| 2015/0220716 A1* | 8/2015 | Aronowitz ............. | G06F 21/32 706/12 |

FOREIGN PATENT DOCUMENTS

| | | |
|---|---|---|
| CN | 104523266 A | 4/2015 |
| EP | 2526859 A1 | 11/2012 |
| WO | 2004030756 A1 | 4/2004 |
| WO | 2014022906 A1 | 2/2014 |

OTHER PUBLICATIONS

Singh, Y.N.; Gupta, P.: ECG to Individual Identification. In: Proc. of the 2nd IEEE BTAS Conf., pp. 1-8 (2008).
Agrafioti, F.; Hatzinakos, D.:ECG Based Recognition Using Second Order Statistics. Communication Networks and Services Research Conference, vol., No. pp. 82,87, 5-8 (2008).
Biel L. et al. ECG analysis: A new approach in human identification. IEEE Trans. Instrum. Meas. 2001;50:808-812.
Shen T. W. PhD. Thesis. University of Wisconsin; Madison, WI, USA: 2005. Biometric Identity Verification Based on Electrocardiogram (ECG).
Wang L. M.S. Thesis. Shan Dong University; Jinan, China: 2005. The Research Based on the ECG Human Identification Technology.
Chiu C.C., et. al. A Novel Personal Identity Verification Approach Using a Discrete Wavelet Transform of the ECG Signal. MUE 2008; Busan, Korea. Apr. 24-26, 2008; pp. 201-206.
Lugovaya T.S. Biometric human identification based on electrocardiogram. [Master's thesis] Electrotechnical University "LETI", Saint-Petersburg, Russian Federation; Jun. 2005.
Kavasaoglu, A. Resit, Kemal Polat b, n, M. Recap Bozkurt a, A novel feature ranking algorithm for biometric recognition with PPG signals, Computers in Biology and Medicine 49, 2014.
Sun, Yi, Yuheng Chen, Xiaogang Wang, and Xiaoou Tang. "Deep learning face representation by joint identification-verification." In Advances in Neural Information Processing Systems, pp. 1988-1996. 2014.
DeepID2 http://blog.csdn.net/stdcoutzyx/article/details/41497545.
Deep Learning and Biometrics http://icb2015.org/media/DL-Bio-final.pdf.
Jin LinPeng, Dong Jun. Deep learning research on clinical electrocardiogram analysis. , 2015, 45(3): 398-416.
Stober, Sebastian, Daniel J. Cameron, and Jessica A. Grahn. Using Convolutional Neural Networks to Recognize Rhythm.
Kaguara, Antony, Kee Myoung Nam, and Siddarth Reddy. "A deep neural network classifier for diagnosing sleep apnea from ECG data on smartphones and small embedded systems."
Zheng, Yi, Qi Liu, Enhong Chen, Yong Ge, and J. Leon Zhao. "Time series classification using multi-channels deep convolutional neural networks." In Web-Age Information Management, pp. 298-310. Springer International Publishing, 2014.

* cited by examiner

METHOD, APPARATUS AND SYSTEM FOR BIOMETRIC IDENTIFICATION

CROSS-REFERENCE TO RELATED APPLICATION

This application is a continuation-in-part of U.S. patent application Ser. No. 14/869,088 titled "Multi-Modal Biometric Identification," filed Sep. 29, 2015, the contents of which is incorporated herein by reference in its entirety.

TECHNICAL FIELD

This disclosure relates in general to identifying a unique individual with biometric measurement signals.

BACKGROUND

Biometric information has been widely used in identification of individuals in various scenarios, such as access control. Such information conventionally includes fingerprints, DNA, eye retinas, facial characteristics, and so forth.

SUMMARY

Disclosed herein are implementations of methods, apparatuses and systems for biometric identification.

In one aspect, the present disclosure includes a method for processing biometric measurement data using a computing device, including receiving at least one biometric measurement record associated with a first biometric measurement generated by contact with a single individual, extracting, by the computing device and for each of the at least one biometric measurement record, feature data including at least one periodic feature extracted from the at least one biometric measurement record, determining, by the computing device, pairing data comprising a plurality of candidate pairs between the feature data and defined profiles associated with a known individual, wherein a candidate pair is associated with one of the at least one periodic feature and one of the defined profiles associated with the known individual, determining, for the candidate pair, a similarity value based on the one of the at least one periodic feature and the one of the defined profiles associated with the known individual, and determining whether a match exists between the single individual and the known individual based on a combination of the similarity values determined for the plurality of candidate pairs.

In another aspect, the present disclosure includes an apparatus comprising a non-transitory memory and a processor. The processor is configured to execute instructions stored in the non-transitory memory to receive at least two biometric measurement signals generated by contact with a single individual, wherein each of the at least two biometric measurement signals is associated with a different biometric modality, extract, for each of the at least two biometric measurement signals, feature data including at least one periodic feature, determine pairing data comprising a plurality of candidate pairs between the feature data and defined profiles associated with a known individual, wherein a candidate pair is associated with one of the at least one periodic feature and one of the defined profiles associated with the known individual, wherein the one of the defined profiles associated with the known individual is indicative of a status of the known individual comprising a movement condition or a health condition, determine, for the candidate pair, a matching result based on similarity of the one of the at least one periodic feature and one of the defined profiles associated with the known individual, and determine whether a match exists between the single individual and the known individual based on a combination of the matching results determined for the plurality of candidate pairs.

In another aspect, the present disclosure includes an apparatus including a body, at least one biometric sensor coupled to the body to produce a biometric measurement when activated by contact with a single individual, a non-transitory memory, a processor, and at least one communication device coupled to the body. The processor is configured to execute instructions stored in the non-transitory memory to receive at least one biometric measurement record associated with the biometric measurement generated by contact with a single individual, extract, for each of the at least one biometric measurement record, feature data including at least one periodic feature extracted from the at least one biometric measurement record, determine pairing data comprising a plurality of candidate pairs between the feature data and defined profiles associated with a known individual, wherein a candidate pair is associated with one of the at least one periodic feature and one of the defined profiles associated with the known individual, determine, for the candidate pair, a similarity value based on the one of the at least one periodic feature and the one of the defined profiles associated with the known individual, and determine whether a match exists between the single individual and the known individual based on a combination of the similarity values determined for the plurality of candidate pairs. The at least one communication device coupled to the body is controlled by the processor to transmit data, to a reader device, indicating that the single individual is the known individual based on a determination that the match exists.

The embodiments or implementations can be configured as executable computer program instructions stored in computer storages such as memory.

BRIEF DESCRIPTION OF THE DRAWINGS

The description here makes reference to the accompanying drawings wherein like reference numerals refer to like parts throughout the several views, and wherein.

DETAILED DESCRIPTION

Figure 1:
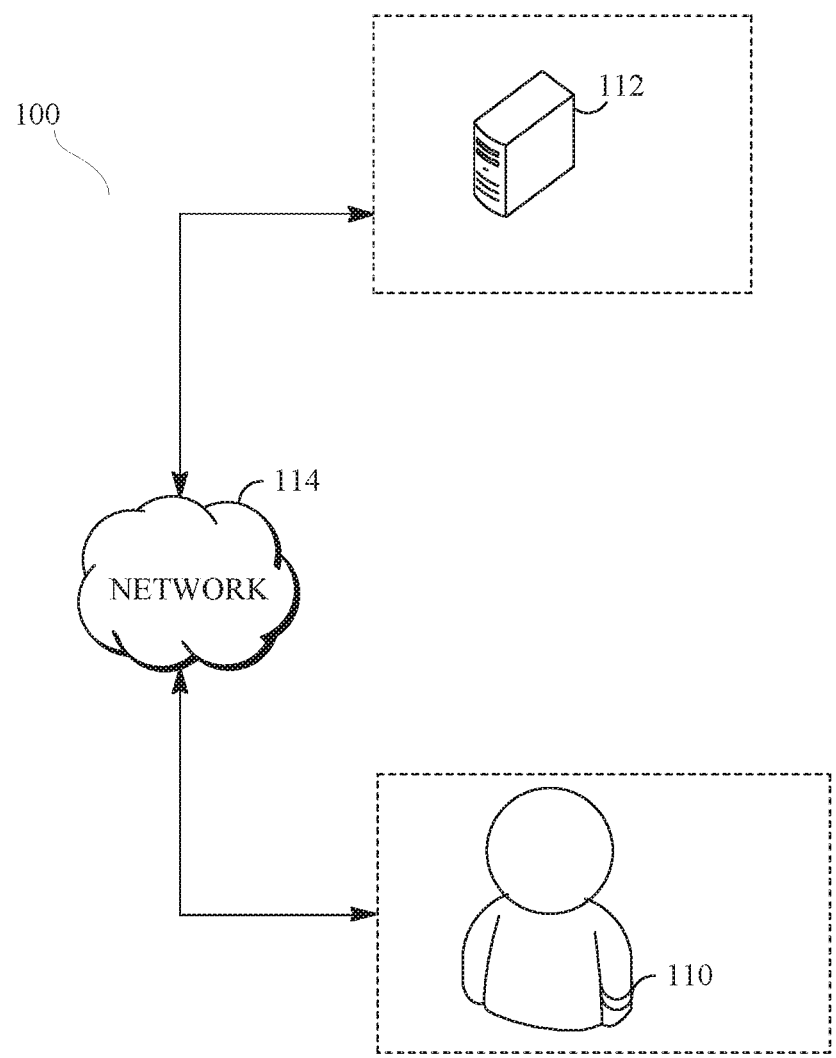
FIG. 1 is a diagram of a system configuration for a biometric identification device and a computer device according to implementations of this disclosure.

Example implementations of the present disclosure will be described below with reference to the accompanying drawings. The same numbers across the drawings set forth in the following description represent the same or similar elements, unless differently expressed. The implementations set forth in the following description do not represent all implementations or embodiments consistent with the present disclosure; on the contrary, they are only examples of apparatuses and methods in accordance with some aspects of this disclosure as detailed in the claims.

A biometric characteristic is applicable as a means to identify a person, if for any individual the characteristic is: universal, meaning that any individual possesses one; easily measured, both technically and procedurally; unique, meaning that no two individuals share identical measurements; and permanent, meaning that the characteristic of the individual does not change over time. Further, when implemented by a wearable device, the biometric measurement signal can have instantaneity that means the measurement should take a small amount of time; accuracy that means the measurement should not misidentify the individual as another person; and security that means the characteristic should not be easily copied or inappropriately possessed by other individuals. The biometric measurement signal used in implementations of this disclosure can be based on, for example, a voice, a hand-writing, a hand geometry, a fingerprint, a palm print, an iris characteristic, a facial characteristic, a bioimpedance signal, an electrocardiogram (ECG) signal, an electroencephalography (EEG) signal, a photoplethysmography (PPG) signal, an electromyography (EMG) signal, or a combination of the above.

A biometric identification is defined as a process of receiving at least one biometric measurement record of a person, and deciding whether the biometric measurement record is an example of that particular person. The biometric measurement record is associated with a biometric measurement signal generated by contact with the person. For example, the at least one biometric measurement record can be determined from an ECG signal. For another example, the at least one biometric measurement record can be determined from more than one modality, for example, an ECG signal and a PPG signal. In some implementations, the biometric identification can be done by comparing characteristics of the received biometric measurement record associated with the person to previously stored data representing characteristics of a known individual (e.g., at least one defined profile), and determining, using a classification model, that whether a match exists between the person and the known individual. The input for the classification model can be, for example, at least one ECG record, and the output of the classification can be, for example, a label of "match" or "not match", or equivalent data.

According to implementations of this disclosure, a method for biometric identification is set forth herein. In some implementations, this method combines both a fiducial point based method and an appearance based method for processing biometric measurement records measured from a user that can include records determined from a multi-modality measurement signal, and uses an ensemble learning model on multiple pairs determined between each of the biometric measurement records measured from the user and each of multiple defined profiles (e.g., template records) associated with a known individual to determine whether the user is the known individual for the purpose of increasing accuracy. For example, the ensemble learning method can include operations of firstly determining a matching result for each of the multiple pairs, and secondly combining the matching result of each pair for the final determination.

FIG. 1 is a diagram of a system configuration 100 for a biometric identification device 110 or a computing device 112 according to implementations of this disclosure.

Biometric identification device 110 as shown is a wearable biometric identification device, namely a device worn around an individual's wrist. However, other devices can be used. For example, device 110 could instead be implemented by another wearable device such as a ring or necklace. Alternatively, device 110 could be implemented as another portable device that is configured to travel with an individual, but not be worn by the individual, such as a device similar in form to a key fob. Computing device 112 can be implemented by any configuration of one or more computers, such as a remote server computer, a personal computer, a laptop computer, a tablet computer, a cell phone, a personal data assistant (PDA), or a computing service provided by a computing service provider, e.g., a website, and cloud computing. For example, certain operations described herein can be performed by a computer (e.g., a server computer) in the form of multiple groups of computers that are at different geographic locations and can or cannot communicate with one another, such as by way of network 120. While certain operations can be shared by multiple computers, in some implementations, different computers are assigned different operations. For example, one or more computing devices, such as a cell phone, could be used to receive and process biometric identification data as described hereinafter, and transmit a signal to biometric identification device 110 and/or elsewhere confirming or denying a match.

In another implementation, an intermediate device (not shown in FIG. 1), can be used to establish a connection to biometric identification device 110 carried or wore by a user, receive a biometric measurement signal of the user from device 110, transmit the biometric measurement signal to computing device 112, such as a remote server, to process the biometric measurement signal. The computing device determines whether the user is a known individual, and transmits a result signal back to the intermediate device. Prior to transmitting the biometric measurement signal to computing device 112, the intermediate device can pre-process the signal. The result signal transmitted back from computing device 112 can be used to indicate the user at the intermediate device, or alternatively, the result signal is further transmitted to biometric identification device 110 by the intermediate device and indicate the user at device 110.

The intermediate device can be a computer or part of a computer, e.g., a cell phone, a PDA, a tablet computer, or a personal computer.

In some implementations, one or more computing devices 112, such as a cell phone, can receive a result signal from a remote device (not shown in FIG. 1), after an identity of the user carrying or wearing biometric identification device 110 is determined. The remote device itself can also be a computer or part of a computer, e.g., another cell phone or a remote server.

Network 150 can be one or more communications networks of any suitable type in any combination, including networks using Bluetooth communications, infrared communications, near field connections (NFC), wireless networks, wired networks, local area networks (LAN), wide area networks (WAN), cellular data networks and the Internet. Biometric identification device 110 and computing device 112 can communicate with each other via network 120. In the implementations described herein, one network 150 is shown. Where more than one computing device 112 is used. In some implementations, each computing device 112 can be connected to the same network or to different networks.

Figure 2:
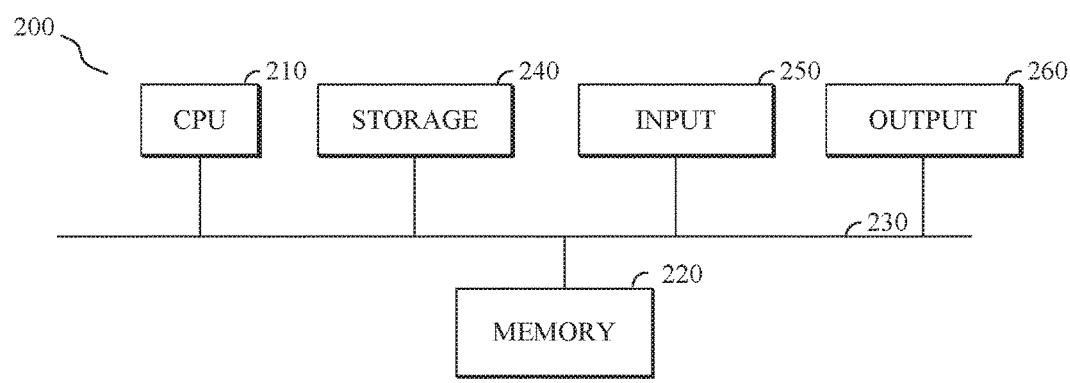
FIG. 2 is a block diagram of a hardware configuration for a biometric identification device or a computing device according to implementations of this disclosure.

FIG. 2 is a block diagram of a hardware configuration for a biometric identification device or a computing device according to implementations of this disclosure. For example, biometric identification device 110 and/or computing device 112 can use hardware configuration 200.

Hardware configuration 200 can include at least one processor such as central processing unit (CPU) 210. Alternatively, CPU 210 can be any other type of device, or multiple devices, capable of manipulating or processing information now-existing or hereafter developed. Although the examples herein can be practiced with a single processor as shown, advantages in speed and efficiency can be achieved using more than one processor.

Memory 220, such as a random access memory device (RAM), a read-only memory device (ROM), an optical disc, a magnetic disc, or any other suitable type of storage device, stores code and data that can be accessed by CPU 210 using a bus 230. The code can include an operating system and one or more application programs processing and/or outputting the data. As will be discussed in detail below, an application program can include software components in the form of computer executable program instructions that cause CPU 210 to perform some or all of the operations and methods described herein. In some implementations, hardware configuration 200 is used to implement computing device 112, in which an application program stored by memory 220 can implement some or all of a process according to FIG. 6 as described in more detail below.

Hardware configuration 200 can optionally include a storage device 240 in the form of any suitable non-transitory computer readable medium, such as a hard disc drive, a memory device, a flash drive or an optical drive. Storage device 240, when present, can provide additional memory when high processing requirements exist. Storage device 240 can also store any form of data, relating or not relating to biometric identification.

Hardware configuration 200 can include one or more input devices 250, such as a keyboard, a numerical keypad, a mouse, a microphone, a touch screen, a sensor, or a gesture-sensitive input device. Through input device 250, data can be input from the user or another device. For example, a gesture-sensitive input device can receive different gestures to switch between different display modes (e.g., heart rate, time, ECG). Any other type of input device 250, including an input device not requiring user intervention, is possible. For example, input device 250 can be a communication device such as a wireless receiver operating according to any wireless protocol for receiving signals. In some implementations, when hardware configuration 200 is used to implement computing device 112, input device 250 can be a wireless receiver for receiving input signals from biometric identification device 110. In another implementation, when hardware configuration 200 is used to implement biometric identification device 110, input device 250 can a wireless receiver for receiving result signals from computing device 112. Input device 250 can output signals or data, indicative of the inputs, to CPU 210, e.g., along bus 230.

Hardware configuration 200 can include one or more output devices 260. Output device 260 can be any device transmitting a visual, acoustic, or tactile signal to the user, such as a display, a touch screen, a speaker, an earphone, a light-emitting diode (LED) indicator, or a vibration motor. If output device is a display, for example, it can be a liquid crystal display (LCD), a cathode-ray tube (CRT), or any other output device capable of providing visible output to an individual. In some cases, an output device 260 can also function as an input device 250—a touch screen display configured to receive touch-based input, for example. Output device 260 can alternatively or additionally be formed of a communication device for transmitting signals. For example, output device 260 can include a wireless transmitter using a protocol compatible with a wireless receiver of biometric identification device 110 to transmit signals from computing device 112 to biometric identification device 110.

Although FIG. 2 depicts one hardware configuration 200 that can implement computer device 112, other configurations can be utilized. The operations of CPU 210 can be distributed across multiple machines or devices (each machine or device having one or more of processors) that can be coupled directly or across a local area or other network. Memories 220 can be distributed across multiple machines or devices such as network-based memory or memory in multiple machines performing operations that can be described herein as being performed using a single computer or computing device for ease of explanation. Although a single bus 230 is depicted, multiple buses can be utilized. Further, storage device 240 can be a component of hardware configuration 200 or can be a shared device that is accessed via a network. The hardware configuration of a computing system as depicted in an example in FIG. 2 thus can be implemented in a wide variety of configurations.

Figures 3A, 3B:
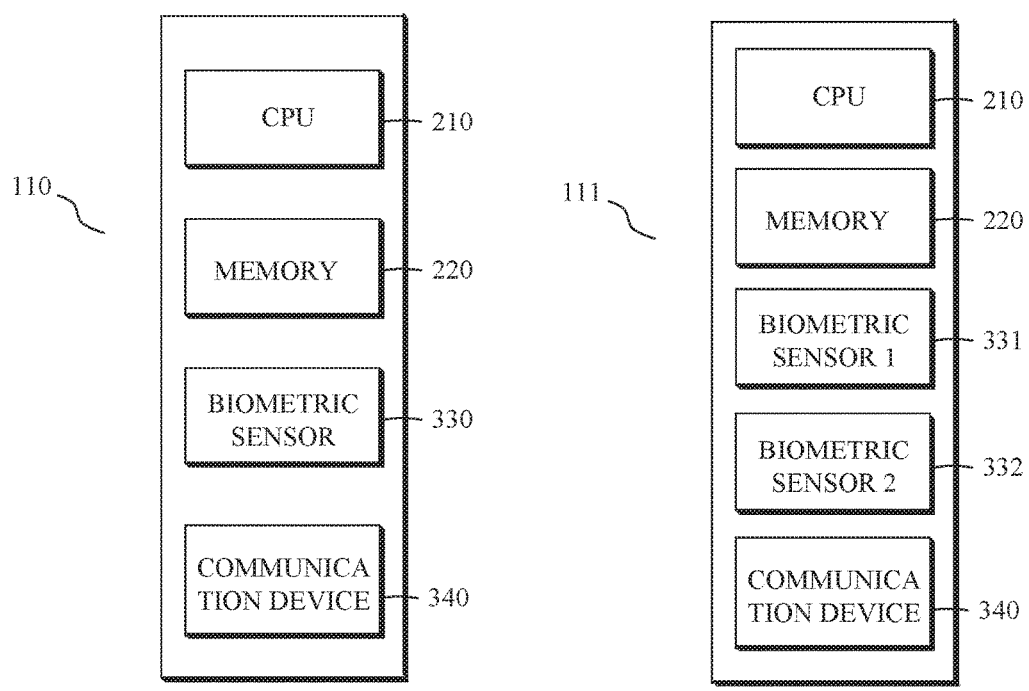
FIG. 3A is a block diagram of a hardware configuration for a biometric identification device or a computing device according to implementations of this disclosure.
FIG. 3B is a block diagram of another hardware configuration for a biometric identification device or a computing device according to implementations of this disclosure.

As a generalized configuration is represented by hardware configuration 200, two more specific hardware configurations for biometric identification device 110 are illustrated as a block diagrams in FIG. 3A and FIG. 3B according to implementations of this disclosure.

In some implementations, as shown in FIG. 3A, biometric identification device 110 comprises CPU 210, memory 220, biometric sensor 330, and communication device 340. CPU 210 and memory 220 can be any implementation as set forth in the description of FIG. 2. Biometric sensor 330 can be configured to be one or more biometric sensors that measure one or more biometric measurement signals of the user, or devices that collect biometric data of the user, e.g., by contacting or interacting with the user. For example, as shown in FIG. 3B, device 110 can include two biometric sensors 331 and 332. The biometric measurement can be a process with or without the user providing indication of starting the measurement to biometric identification device 110 and/or inputting data during the measurement process, in which the indication or data, if incurred, is transmitted via communication device 340. Biometric sensors 330, 331 and 332 can be a microphone, a camera, a touch screen, a fingerprint reader, an iris scanner, a bioimpedance sensor, an ECG sensor, an EEG sensor, a PPG sensor, an EMG sensor, or a combination of a plurality of the abovementioned sensors.

Communication device 340 is configured to input and/or output signal to biometric identification device 110, which can be any implementation of input device 250 and/or output device 260 or a combination thereof. In some implementations, communication device 340 further includes a display for presenting output to indicate the successful identification of the user. In a further implementation, the display is a touch screen display configured to receive touch-based input, for example, in manipulating data outputted thereto. In another implementation, communication device 340 can be configured to receive a signal from computing device 112, an intermediate device, or a remote device as set forth in aforementioned description.

A configuration of biometric identification device 110 is described in more detail with reference to FIG. 4 and FIG. 5.

Figure 4:
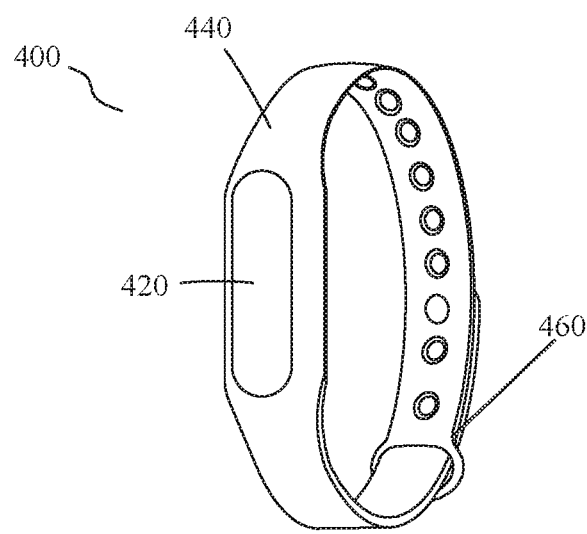
FIG. 4 is a diagram of an example biometric identification device according to implementations of this disclosure.

FIG. 4 is diagram of an example biometric identification device according to implementations of this disclosure. In this example, device 110 is shown as a wristband device 9-400. Although wristband device 400 is shown as having a module 420 secured to a wrist band 440, other devices that can be worn on an individual's body can be used, such as wearables on the user's arms, wrists or fingers. The module 420 of wristband device 400 can include, for example, CPU 210, memory 220, one or more biometric sensors 330 and one or more communication devices 340. Securing mechanism 460 can also be included to secure band 440 to the user.

Figure 5:
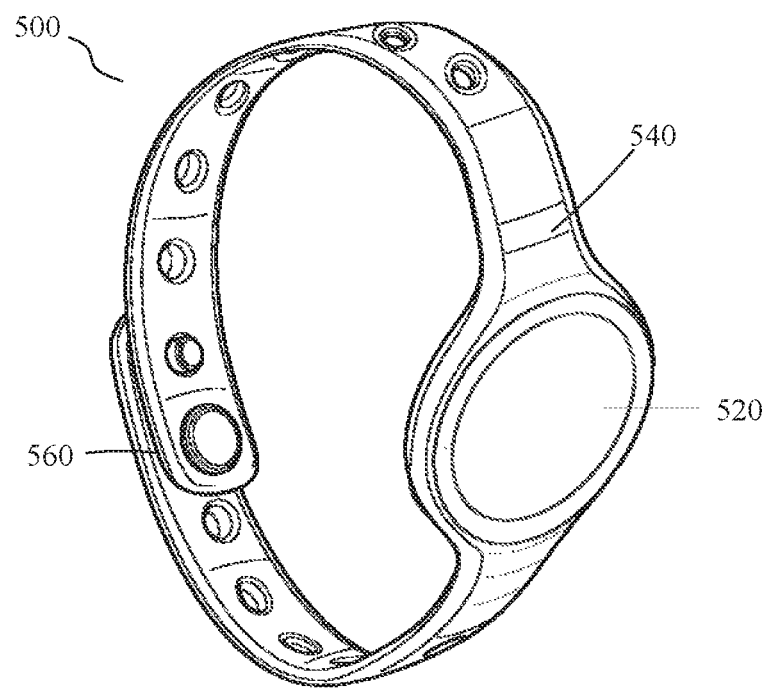
FIG. 5 is a diagram of an example biometric identification device according to implementations of this disclosure.

FIG. 5 is diagram of an example biometric identification device according to implementations of this disclosure. In this example, device 110 is shown as a "smart" watch 500.

Although watch 500 is shown as having a module 520 secured to a wrist band 540, other devices that can be worn on an individual's body can be used, such as wearables on the user's arms, wrists or fingers. The module 520 of watch 500 can include, for example, CPU 210, memory 220, one or more biometric sensors 330 and one or more communication devices 340. Securing mechanism 560 can also be included to secure band 540 to the user.

In some implementations, securing mechanism 460 and/or 560 is a slot and peg configuration. In other implementations, securing mechanism 460 and/or 560 can include a snap-lock configuration. It will be apparent to one skilled in the art in view of the present disclosure that various configurations can be contemplated for securing mechanism 460 and/or 560.

Figure 6:
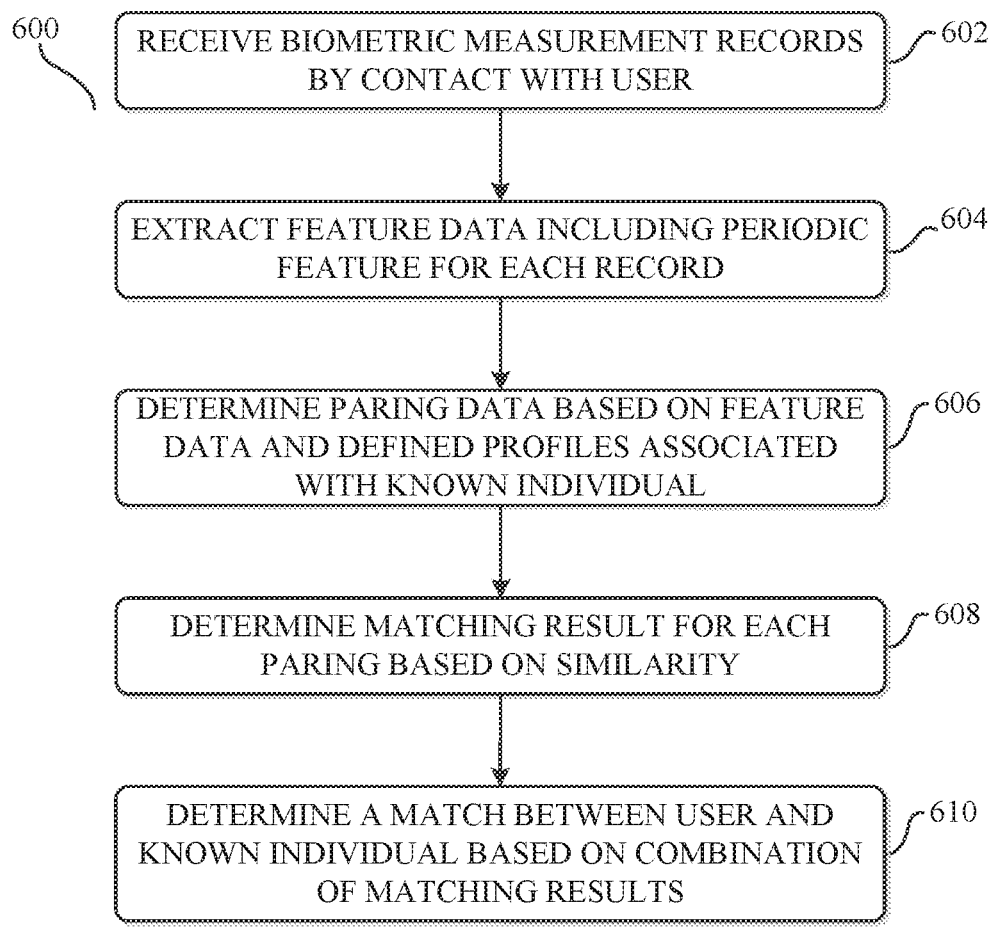
FIG. 6 is a flowchart showing an example process of processing biometric measurement signals according to implementations of this disclosure.

FIG. 6 is a flowchart showing an example process of processing biometric measurement records according to implementations of this disclosure. The operations described in method 600 can be performed at one or more computing devices, e.g., a computing device 112 such as a remote server, or an intermediate device such as a cell phone, or at the biometric identification device 110, or a combination of the above. When an operation is performed by one or more such computing devices, it is completed when it is performed by one such computing device. The operations described in method 600 can be implemented in memory 220 including program instructions executable by CPU 210 that, when executed, cause CPU 210 to perform the operations.

It should be understood that method 600 can also be performed by, for example, biometric identification device 110, computing device 112, or by multiple devices. For simplicity of explanation, method 600 is described in the example below as performed by computing device 112. Accordingly, biometric measurement records can be received at computing device 112 from biometric identification device 110 through, for example, communication device 340 at operation 602. For example, the biometric measurement records can include biometric measurement signals (e.g., ECG signals or PPG signals) received at the computing device 112, which can include, for example, data about the biometric measurement signals or associated with the biometric measurements. For example, biometric measurement records can include characteristics based on biometric measurements performed in association with the user, and can be used to identify the user. In some implementations, the biometric measurement ends after a defined period of time lapses. In other implementations, the biometric measurement ends when the contact of the individual with a sensor ends.

At operation 602, biometric measurement records associated with a first biometric measurement, generated by biometric identification device 110 contacting with a user, are received. The biometric measurement records can be determined from any signal measured and generated by any kind of biometric sensor set forth herein. The receiving is defined herein as receiving, inputting, acquiring, retrieving, obtaining, reading, accessing, determining, or in any manner inputting a biometric measurement record to computing device 112. In some implementations, a biometric measurement record can be associated with a single biometric modality, for example, an ECG signal. Accordingly, the biometric measurement records can include, for example, M number of ECG signals measured by biometric identification device 110 by contacting with the user for 30 seconds, during which each ECG signal measurement lasts for 5 seconds, resulting in 6 ECG signals (i.e., M=6). In some implementations, the biometric measurement records can include two or more biometric measurement records, each biometric measurement record associated with a different biometric modality. Accordingly, the feature data sets for multi-modality biometric identification can be determined, for example, by combining the feature data determined for each of the two or more biometric measurement records. The multi-modality biometric measurement records can include, for example, an ECG record, a PPG record, and/or a bioimpedance record.

In some implementations, the biometric measurement record can be received via biometric sensor 330, 331 or 332, by computing device 112, such as biometric identification device 500. In some implementations, the biometric measurement record can be received via communication device 340 by computing device 112, such as a server or a personal computer. In some implementations, the biometric measurement record can be received via communication device 340 by an intermediate device, such as a cell phone or a tablet computer, which further can transmit the signal to computing device 112, such as a server or another cell phone.

At operation 604, for each of the biometric measurement records, feature data including periodic features extracted from the biometric measurement records is extracted by computing device 112. In some implementations, the extracted feature data can be aggregated in a form of a feature data set. For example, as a result of the M biometric measurement records or signals, a total of M feature data sets can be extracted. A feature data set is defined to be a set of feature data that is extracted from and represents characteristics of each of the received biometric measurement records. For example, the received biometric measurement records can present periodical features or characteristics, such as cycles or periods. Other data representing other features or characteristics of the received biometric measurement records can be included in the extracted feature data sets as well. In some implementations, the biometric measurement signal can be an ECG signal that includes one or more complete ECG periodic fragments, such as PQRST cycles. A PQRST cycle of an ECG signal is defined as a portion of the ECG signal that represents one complete heartbeat, which consists of a P-wave, a QRS complex and a T-wave connected in temporal order. The peak of a QRS complex is defined as an R-peak. For example, after detecting R-peaks, PQRST cycles can be extracted from the signal based on R-peaks by, for example, directly taking signal data around the R-peaks, or any other technique that can be used to extract ECG periodic fragments. In some implementations, an extracted periodic fragment can be represented by an image, a vector, or other data structures.

In some implementations, prior to extracting the M feature data sets, the biometric measurement record can be pre-processed. For example, the intermediate device can pre-process the biometric measurement record prior to transmitting the same to computing device 112, at which the M feature data sets are extracted. In some implementations, the pre-processing of the biometric measurement record can be performed at computing device 112 other than the intermediate device, such as biometric identification device 110.

The pre-processing includes a number of manipulations to the biometric measurement record to ensure data integrity and to prepare the signal for subsequent processing. The type of pre-processing varies according to type of signal, but generally involves removing noisy data from raw signals (e.g., denoising) measured by the sensors. In some implementations, the pre-processing can include removing baseline wander in the raw signals (e.g., adjusting the input signals during one measurement cycle to a common baseline). In another implementation, the pre-processing can include filtering, such as using a band pass filter, which can remove any undesirable data shifts that occurred while the raw signals were being measured and to reduce the presence of data outside of a range to be observed (e.g., outliers).

In some implementations, the feature data sets can be extracted from the biometric measurement records using one or more different techniques. For example, the biometric measurement records can be one or more PQRST cycles extracted from an ECG signal, and to obtain features of the extracted PQRST cycles, various analysis methods can be applied. In general, a fiducial point based approach (also called a rule based approach) detects values associated with various segments of a signal delineation or waveform, such as durations, intervals, amplitudes, magnitudes, or angle features, while an appearance based approach detects the shapes of the signal. It can be the shape in the time domain, such as a wave fragment, or the shape in the frequency domain, for example, the output from the combination of an autocorrelation (AC) and a discrete cosine transform (DCT) of the signal. Each of those approaches to feature extraction has its strengths and weaknesses. While the fiducial point based approach is well-adjusted to changes in heart rate (e.g., its accuracy does not significantly decrease with heart rate changes), it requires a good detection algorithm, it is slow, and it is sensitive to noise. In contrast, the frequency domain, appearance based approach does not need to detect various segments of the signal, so it is faster. The appearance based approach is also less sensitive to noise, but is more sensitive to arrhythmia fragments.

In some implementations, for the fiducial point based approach, feature extraction can be achieved using calculations including one or more of a spectral based feature, wavelet, DCT, power density, and ensemble empirical mode decomposition (EEMD). The features can be, for example, the amplitude and duration values themselves, combinations of the amplitude and/or duration values, or values derived using the amplitude and/or duration values through, for example, an AC or periodicity transform (PT). One feature of the fiducial point based approach can be, for example, heart rate variability (HRV), which is the variation of beat-to-beat intervals (i.e., the time from R to R per cycle).

In some implementations, for the appearance based approach, feature extraction can include steps of windowing, where the pre-processed ECG signal or trace is segmented into non-overlapping windows so that each window has a length sufficient to encompass multiple cycles, performing an AC, where normalized autocorrelation of each window can be estimated, and performing a DCT. The extracted features can include, for example, one or more PQRST cycles, a certain number of the highest DCT coefficients, how many DCT coefficients are associated with certain power values, a fitted curve for the points defining peaks or valleys in the DCT plot, and so forth. The appearance based approach can also be a parameterization of the curves representing the shapes of each period.

In some implementations, dimensionality of the features, extracted using either the fiducial point based approach or the appearance based approach, can be reduced or encoded using a dimension reduction technique, such as a principal component analysis (PCA), a linear discriminant analysis (LDA) and/or an independent component analysis (ICA). Other existing techniques of dimensionality reduction can also be used.

At operation 606, pairing data, which is based on the feature data and defined profiles associated with a known individual, is determined by the computing device. The pairing data can be determined between the periodic features and the defined profiles associated with the known individual. In some implementations, the known individual can be associated with more than one defined profiles, for example, N number of defined profiles. For example, the pairing data can be one or more candidate pairs determined between each of the M feature data sets associated with the user and each of the N defined profiles associated with the known individual, yielding a total of M*N candidate pairs.

A defined profile can include data that represents features or characteristics from past biometric measurement records associated with the known individual. The data for the defined profile can include data extracted from the past biometric measurement records using the same device or received from a remote database (e.g., database in a cloud). In some implementations, the defined profiles associated with the known individual can be of the same structure as the feature data set associated with the user, which can be implemented or stored as templates to be used in further operations as described hereinafter.

Figure 10A:
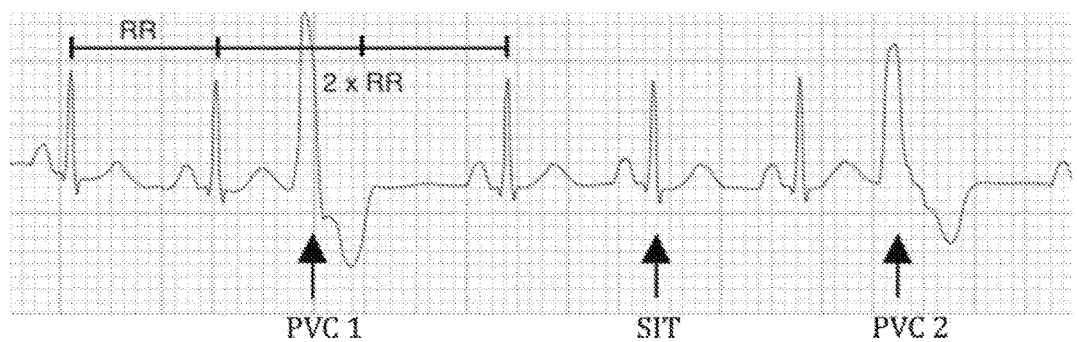
FIG. 10A is a diagram showing an example ECG signal of a person with Premature Ventricular Contraction (PVC) according to implementations of this disclosure.
Figure 10B:
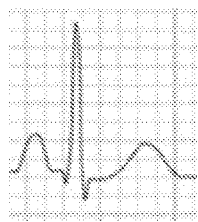
FIG. 10B is a diagram showing an example status extracted from the ECG signal in FIG. 10A according to implementations of this disclosure.
Figure 10C:
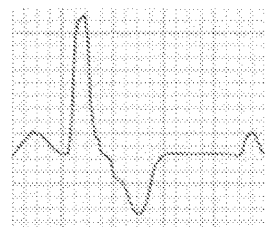
FIG. 10C is a diagram showing another example status extracted from the ECG signal in FIG. 10A according to implementations of this disclosure.

For the reason that signal morphology can change for each person during different status or health conditions, multiple defined profiles (e.g., template records) can be maintained for the known individual. Each status can have one or multiple profiles. In some implementations, some or each of the N defined profiles can be associated with templates collected at different times, but indicating a same status or health condition for the known individual. In some implementations, each of the N defined profiles can be indicative of a different status or a health condition of the known individual. For example, the different status can be a motion status of the user, such as running, walking, standing, or sitting. For example, one or more signals collected from at least one activity sensor, such as an accelerometer or a gyroscope, can be used to identify the motion status of the user. For example, a pattern recognition algorithm can be used and trained to automatically identify a motion status of running, walking, standing, etc., before applying a matching algorithm. In this example, each motion status or health condition has at least one defined profile. In another example, the health condition can include having a heart a heart disease, which can be triggered by a disease event, such as a Premature Ventricular Contraction (PVC) event or a Premature Atrial Contraction (PAC) event. For example, FIG. 10A shows a diagram of an ECG signal of a person with PVC according to implementations of this disclosure. In the diagram of FIG. 10A, the ECG is recorded for a person during occasionally PVC attack while sitting, showing multiple morphologies. The RR in FIG. 10A indicates a distance between two R-peaks. Between another two R-peaks with another distance of two times of RR, a pattern indicative of a PVC event, namely "PVC 1", is shown. Another PVC event named as "PVC 2" is also shown in another portion of the ECG record. FIG. 10C is a complete cycle of "PVC 2" including its surrounding signal portion. Between "PVC 1" and "PVC 2", another portion of the ECG record labeled as "SIT" is shown, which is indicative of a sitting status of the user, and its complete cycle is further illustrated in FIG. 10B.

At operation 608, for each candidate pair, a matching result based on similarity of a periodic feature and a corresponding defined profile is determined. In some implementations, the candidate pair can include a feature data set extracted from the user and a defined profile associated with the known individual, and the matching result for the candidate pair can be a text, a numerical value, a symbolic value, or any other type of data indicative of a meaning of "match" or "not match" between the feature data set and the defined profile included in the candidate pair. For example, if the matching result is "match" or equivalent data, the feature data set and the defined profile can be considered to be associated with a same person; otherwise, if the output label is "not match" or equivalent data, the feature data set and the defined profile can be considered to be associated with different persons.

In some implementations, the matching result is determined based on similarity of the corresponding periodic feature and the corresponding defined profile, for example, a similarity value or a matching score, the process of which is set forth as two steps in the following description.

Firstly, for the candidate pair, the similarity value is determined based on characteristics determined from the candidate pair. For example, the characteristics can include a distance (e.g., Euclidean distance) determined between the feature data set and the defined profile. In another example, the characteristics can be one or more parameters determined from a probability based method. In another example, the characteristics can be one or more parameters determined from a learning based method. In another example, the learning based method can be an LDA. Accordingly, the similarity value can be, for example, a value determined from the Euclidean distance between the feature data set and the defined profile (using a distance measure or parameter), a value determined from the parameters of the probability based method (using a probability based measure or parameter), or a value determined from the parameters of the learning based method (using a learning based measure or parameter), such as a LDA.

Secondly, for the candidate pair, the matching result is determined based on the similarity value using a classification model. In some implementations, the classification model can be a threshold model. For example, the threshold model can include the following steps:

First, for the candidate pair, it is determined that whether the similarity value is greater than a predetermined value, for example, a threshold value.

Second, if the similarity value is greater than the threshold value, the matching result is determined for the candidate pair, for example, a text of "match" or any other type of data indicative of the same meaning.

In some implementations, the classification model can be a machine learning model. For example, the machine learning model can be a supervised learning model, such as a support vector machine (SVM) model, or a random forest model.

At operation 610, it is determined whether a match exists between the user and the known individual based on a combination of the matching results determined for the candidate pairs. As previously discussed, the matching results can be based on the similarity scores. In some implementations, if one or more of the candidate pairs has a very high similarity score, the user can be considered to be the known individual. In some implementations, an ensemble learning model can be used. For example, the ensemble learning model can be a majority voting model, in which the match between the user and the known individual is determined to exist if, for example, a percentage of the candidate pairs having a same matching label indicative of "matching" between the feature data set and the defined profile of each candidate pair over a total number of the candidate pairs is greater than a predetermined value, for example, 50%. In another example, the ensemble learning model can be a learning based model trained from the combined matching results and features extracted from the candidate pairs. The features extracted from the candidate pairs used in the learning based model can include, for example, a distribution of the similarity values associated with the candidate pairs.

According to implementations of this disclosure and foregoing description, the defined profiles associated with the known individual in operation 606-610 can be extracted in a process set forth in the following description.

Biometric measurement records associated with a second biometric measurement generated by contact with the known individual are received, for example, prior to operation 602. The second biometric measurement can be either the same or difference biometric measurement in which biometric measurement records associated with the user are received. The second biometric measurement can also be performed by either a same computing device or different computing devices, at a same time or different times with respect to the biometric measurement for the user.

Then, by the computing device and for each of the biometric measurement records associated with the second biometric measurement, the defined profiles including periodic features are extracted from the biometric measurement records associated with the second biometric measurement. The defined profiles can be stored as template records associated with the known individual. In some implementations, the extracted defined profiles can be of the same structure as the feature data extracted from the biometric measurement associated with the user. In some implementations, the defined profiles, after extraction, can be stored in the computing device or transmitted and stored in a different computing device, in which the computing devices can be biometric identification device 110 or computing device 112 including an intermediate device.

Figure 7:
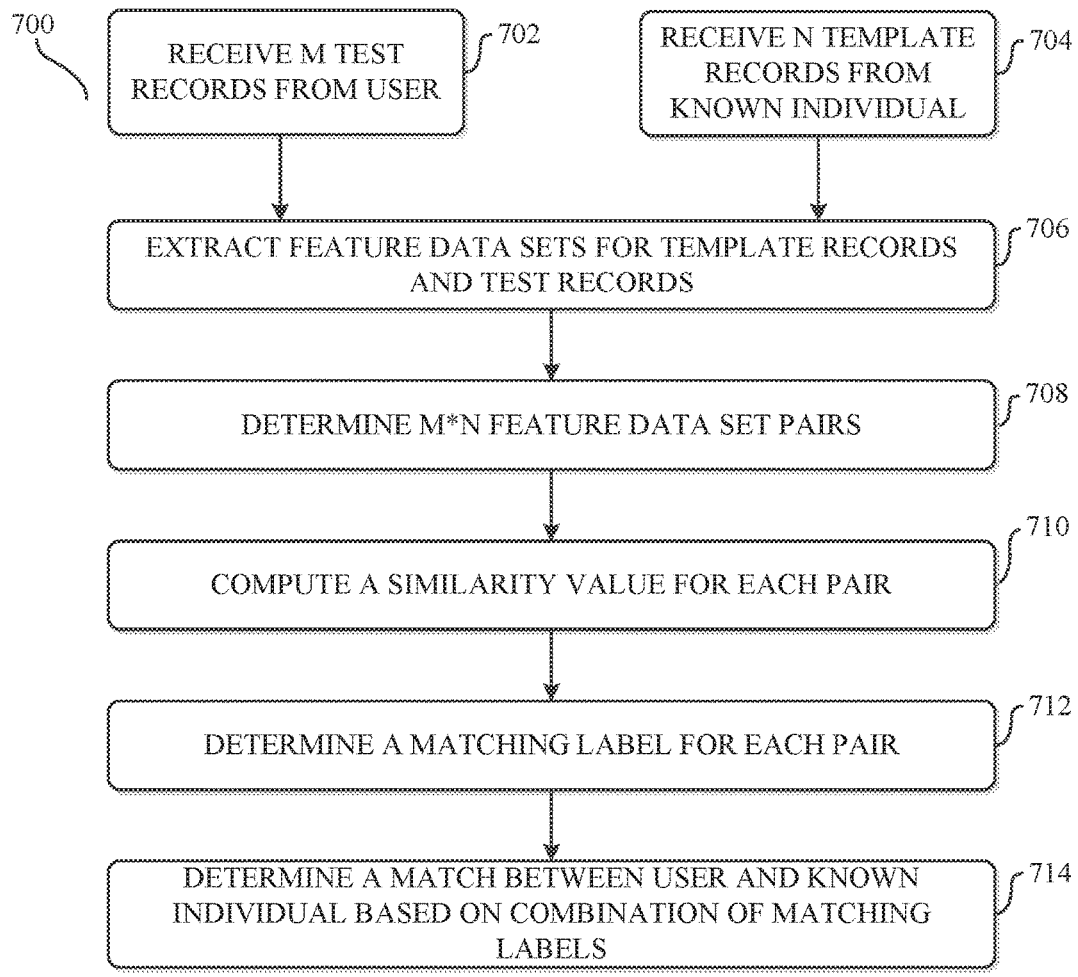
FIG. 7 is a flowchart showing another example process of processing biometric measurement signals according to implementations of this disclosure.

As an example according to implementations of this disclosure, FIG. 7 shows a flowchart of an example process of processing biometric measurement data for identifying a user. In this example, multiple (M>1) test records measured from the user and multiple (N>1) template records associated with a known individual are used.

At operation 702, M biometric measurement records ("test records") measured from the user are received. The M test records of the user can be measured during a biometric identification process, such as when the user is wearing biometric identification device 110 with biometric sensors 331 and 332. The test records can be received by biometric identification device 110, or by another computing device 112 communicating with device 110 through communicating device 340. In the biometric identification process, the entire measurement can last, for example, 30 seconds, and each record (signal) can be determined as a signal lasting for, for example, 5 seconds, in which case the number of records M is 6 (i.e., M=6). The M records can also be measured from, for example, a multi-modality biometric measurement, in which case M records of different modalities (e.g., ECG, PPG, and other types of measurement signals) are received.

At operation 704, N biometric measurement template records ("defined profiles") associated with the known individual are received. The receiving can be performed at a time, for example, different from the biometric identification process, such as before the biometric identification process. The N template records associated with the known individual, also referred to herein as defined profiles associated with the known individual, can be pre-stored in, for example, storage 240 of biometric identification device 110, or storage 240 of another computing device 112 (including an intermediate device) communicating with device 110 through communicating device 340. The template records can be associated with, for example, one or more motion status ("movement condition") of the known individual, such as sitting, walking and running. The template records can also be associated with one or more health condition of the known individual, such as a PVC event or a PAC event. In another example, there can be more than one template record associated with the same motion status or the same health condition associated with the known individual.

At operation 706, N feature data sets (e.g., N template feature data sets) are extracted for the N received template records, and M feature data sets (e.g., M test feature data sets) are extracted for the M received test records. The extraction process for the N template feature data sets and the M test feature data sets can use the technique described in operation 604. In some implementations, the N template feature data sets and the M test feature data sets can be extracted at different times. For example, the N template feature data sets can be extracted and stored in storage 240 of biometric identification device 110 or storage 240 of another computing device 112 (including an intermediate device) at a time before the extracting the M test feature data sets in the biometric identification process. The extraction process for both feature data sets can be performed by a same device or different devices, such as biometric identification device 110 or computing device 112 (including an intermediate device). As an optional step, dimension reduction techniques, such as PCA, can be applied to the feature data sets to reduce dimensionality.

At operation 708, a candidate pair is determined between each of the N template feature data sets and each of the M test feature data sets, yielding M*N candidate pairs. The candidate pair process can be performed by a same device or different devices, such as biometric identification device 110 or computing device 112 (including an intermediate device).

At operation 710, for each candidate pair, a similarity value, such as a matching score, is computed. The matching score can represent a level of similarity for each candidate pair. The computing process has been set forth in the description of operation 608 and can be performed by a same device or different devices, such as biometric identification device 110 or computing device 112 (including an intermediate device).

At operation 712, for each candidate pair, a classification model is used to determine a matching label (i.e., a matching result) based on the similarity value. The matching label can represent whether the template feature set matches the test feature set in the same candidate pair. The classification model has been set forth in the description of operation 608 and can be implemented by a same device or different devices, such as biometric identification device 110 or computing device 112 (including an intermediate device). For example, the classification model can be a threshold model.

At operation 714, the matching labels of the candidate pairs are combined to determine a match between the user and the known individual, using an ensemble decision model. The ensemble learning model has been set forth in the description of operation 610 and can be implemented by a same device or different devices, such as biometric identification device 110 or computing device 112 (including an intermediate device). For example, the ensemble learning model can be a majority voting model. In another example, the ensemble learning model can be a learning based model, which can be trained from the matching score distribution and the matching labels of the candidate pairs.

According to implementations of this disclosure, for a plurality of candidate pairs, for example, M*N candidate pairs with M and N defined in foregoing description, operation 608 can be performed for every candidate pair of a feature data set extracted from the user and a defined profile associated with a known individual, and a matching result, or a matching label, is obtained for the candidate pair. For example, in a testing phase in actual use, a candidate pair of two signals, for example, ECG signal 1 and ECG signal 2, are input to computer device 112 to determine a matching label between them.

Figure 8:
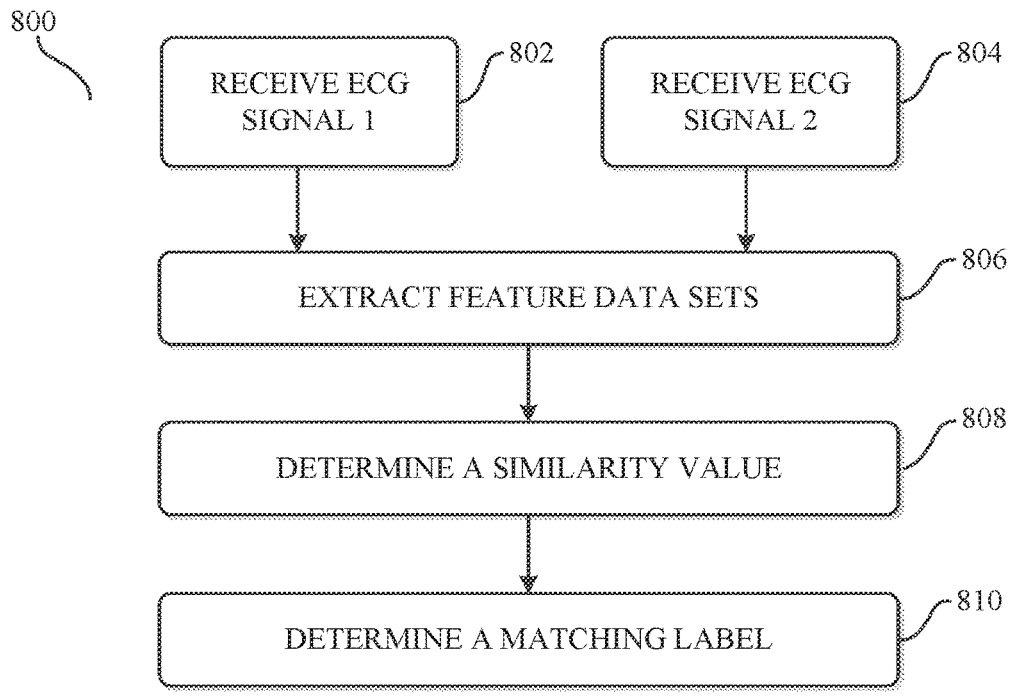
FIG. 8 is a flowchart showing an example process of determining a matching label for a pair of biometric measurement signals according to implementations of this disclosure.

As shown in FIG. 8, in some implementations, this pair matching process can include operations 802-810 as set forth in the following description. In this example, for simplicity, only one pair is described. For each input signal, operations 802-810 can be implemented by process 600 as previously described.

At operation 802 and 804, two ECG signals, ECG signal 1 and ECG signal 2, are received, respectively. For example, ECG signal 1 can be a template signal measured from the known individual ("a defined profile" for the known individual) and ECG signal 2 can be a test signal measured from the user.

At operation 806, feature data sets are extracted for ECG signal 1 and ECG signal 2, respectively. As an optional step, dimension reduction techniques, such as PCA, can be applied to the feature data sets to reduce dimensionality.

At operation 808, a similarity value is determined between the two ECG signals.

At operation 810, a matching label is determined for ECG signal 1 and ECG signal 2 based on a classification model, also referred to hereinafter as a classifier. The classification model can be, for example, trained and stored for use in another biometric identification process set forth in later description.

Figure 9:
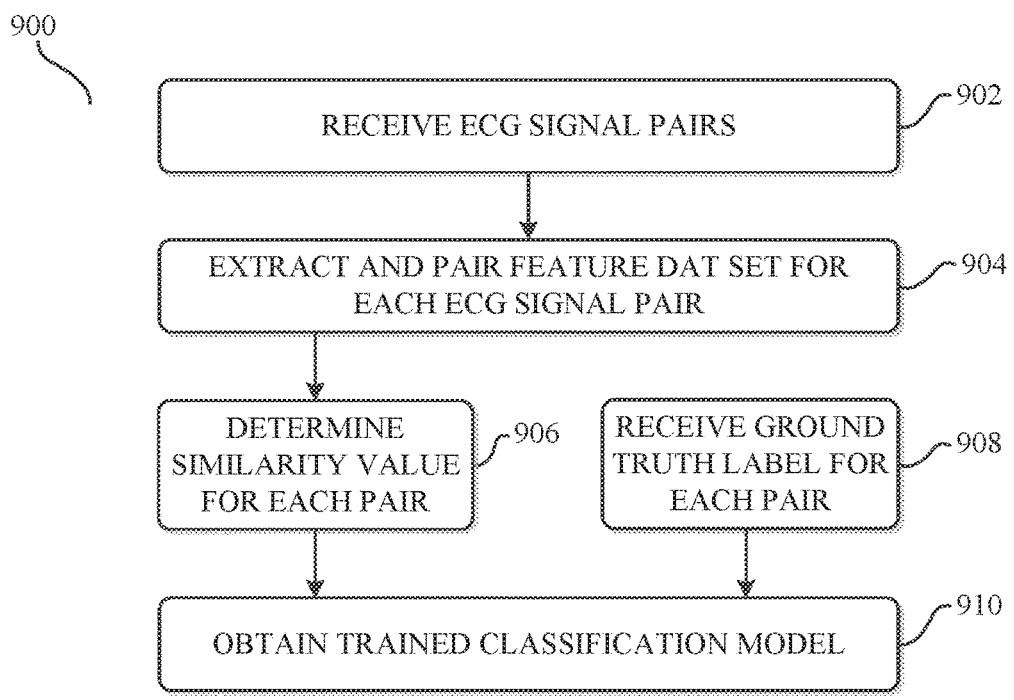
FIG. 9 is a flowchart showing an example process of training a classification model during a setup process according to implementations of this disclosure.

In some implementations according to this disclosure, a trained machine learning model can be used as the classification model in operations 608, 712 and 810. The machine learning model can be, for example, a supervised learning model which can be trained during a setup process shown as an example flowchart in FIG. 9 according to implementations of this disclosure. The setup process can be performed, for example, prior to the testing phase or practical use.

At operation 902, a plurality of ECG signal pairs is received. For each ECG signal pair including a first signal and a second signal, both signals can be measured from, for example, either the same individual or different individuals. For example, the first signal can be a template signal measured from the known individual and the second signal can be a test signal measured from the user.

At operation 904, for the two signals within each ECG signal pair, two feature data sets (e.g., two feature vectors) are respectively extracted and paired, with the two feature data sets extracted according to the description set forth in operations 604, 706 and 806. The extracted feature data sets can include features of, for example, AC-DCT parameters, PQRST fragments, fiducial points, or other features set forth herein. As an optional step, dimension reduction techniques, such as PCA, can be applied to the feature data sets to reduce dimensionality.

At operation 906, a similarity value, such as a matching score, is determined for each pairing data, using a same technique set forth in operations 608, 710 and 808. For example, the similarity measure can be a distance measure of the two feature vectors (e.g., Euclidean distance), or can be a learning based measure based on the two feature vectors (e.g., LDA parameters).

At operation 908, for each candidate pair, a ground truth label associated with the ECG signal pair is received. The ground truth label is a predetermined label representing the true relationship between the two individuals (e.g., "match" or "not match").

At operation 910, for each candidate pair, the similarity value and the ground truth label are inputted into the classification model for training. In some implementations, the classification model can, for example, determine a matching label for the pairing data based on the similarity value. The matching label can be, for example, compared with the ground truth label of the pairing data and based on the comparison, parameters of the classification model can be updated, to the effect that after the update the classification model will have a higher probability to determine a second matching label for the same pairing data the same as the ground truth label associated with the pairing data (i.e., a "correct" classification) in a future training process. The classification model can be, for example, a threshold model, or a supervised machine learning model, such as a SVM or a random forest model.

Operation 902-910 can be repeated for at least one time for each ECG signal pairs, until the rate of correct classifications reaches a pre-determined level, such as, for example, 90%. In some implementations, this process can be repeated until a pre-determined running duration is reached without the rate of correct classification reaching the pre-determined level. When the repeated process ends, the classification model completes the setup process and is ready for practical use. In some implementations, the trained classification model can be stored for future biometric identification.

In some implementations, for processes 700, 800 and 900, either in a training process or in practical use, the inputted template records in operation 702, test records in operation 704, ECG signal 1 in operation 802, ECG signal 2 in operation 804, and the ECG signal pairs in operation 902 are not limited to a single modality, with all other operations in the abovementioned processes the same. For example, for a multi-modality measurement, the inputted signal in the abovementioned processes can include at least one selected from the group of ECG records, PPG records, bioimpedance records, EEG records, EMG records, or any other biometric records. Different feature data can be extracted from each modality of records and can be further aggregated or concatenated into a single feature data set for the records associated with the multi-modality biometric measurement as, for example, a vector.

In some implementations, biometric identification device 110 can be configured to have full capability of executing the entire of process 600, e.g., a "smart" watch shown in FIG. 5. In such implementations, at least one biometric sensor (e.g., biometric sensor 331 or 332) can be coupled to body 520 to produce biometric measurement signal ("signal" is used interchangeably with "record" hereinafter) s when activated by contact with the single individual, and at least one communication device (e.g., communication device 330) can be coupled to body 520 and controlled by CPU 210 to transmit the result data s to a reader device indicating the biometric identification result. In such implementations, CPU 210 is configured to execute instructions stored in memory 220 to receive at least one biometric measurement record associated with a first biometric measurement generated by contact with a single individual, extract feature data including at least one periodic feature for each of the at least one biometric measurement record, determine pairing data based on the feature data and defined profiles associated with a known individual wherein each candidate pair is between each of the at least one periodic feature and each of the defined profiles associated with the known individual, determine a matching result based on similarity of a corresponding periodic feature and a corresponding defined profile, and determine whether a match exists between the single individual and the known individual based on a combination of the matching results determined for the candidate pairs.

In some implementations, the at least one biometric measurement record can include two or more biometric measurement records, each of the two or more biometric measurement records associated with a different biometric modality, in which the two or more biometric measurement records can include a first biometric measurement record and a second biometric measurement record, and the first and second biometric measurement records can be selected from a group comprising an ECG record, a PPG record, or a bioimpedance record. In some implementations, if two or more biometric measurement records associated with different biometric modalities are used for multi-modality biometric identification, the feature data can be determined by combining the feature data determined for each of the two or more biometric measurement records. In some implementations, the feature data can be a feature data set including the at least one periodic feature and other data (e.g., matching score distributions) extracted from each of the at least one biometric measurement record using at least one technique, such as a fiducial point based approach or an appearance based approach. In some implementations, the extraction process for the feature data set can further include removing noisy data and outlier data from each of the at least one biometric measurement record. In some implementations, each of the defined profiles associated with the known individual can be indicative of a different status or a health condition of the known individual, in which the different status can include at least one of running, walking, standing, and sitting, and the health condition can include a Premature Ventricular Contraction (PVC) event or a Premature Atrial Contraction (PAC) event.

Optionally, in some implementations, the aforementioned biometric identification device 110 can further have the capability of generating the defined profiles in a setup process. In such implementations, CPU 210 is configured to execute instructions stored in memory 220 to receive at least one biometric measurement record associated with a second biometric measurement generated by contact with the known individual, and extract, for each of the at least one biometric measurement record associated with the second biometric measurement, the defined profiles including at least one periodic feature extracted from the at least one biometric measurement record associated with the second biometric measurement.

In some implementations, biometric identification device 110 can be configured to have partial capability of executing the entire of process 600, e.g., a wristband shown in FIG. 4. Such device can execute some operation of process 600, e.g., operation 602, and have the rest of process 600 executed by an external server, being either computing device 112 or an intermediate device. In such implementation, biometric sensor 330 can be a biometric sensor coupled to body 420 to produce at least one biometric measurement record when activated by contact with a user. Communication device 340 can be one or more communication device coupled to body 420 controlled by CPU 210 to wirelessly transmit the at least one biometric measurement record received from the at least one biometric sensor to an external server, wherein feature data including at least one periodic feature is extracted from the at least one biometric measurement record, wirelessly receive a first signal from the external server indicative of a biometric identification data generated from the at least one biometric measurement record, wherein the first signal is determined based on candidate pairs determined based on the feature data and defined profiles associated with a known individual, and a matching result is determined for each candidate pair based on similarity of a corresponding periodic feature and a corresponding defined profile to further determine whether a match exists indicating the single individual is the known individual based on a combination of the matching results determined for the candidate pairs, and wirelessly transmit a second signal to an identification device in response to a match indicating that the single individual is the known individual.

In some implementations, communication device 340 can include a first wireless communication device configured to wirelessly transmit the at least one biometric measurement record from biometric sensor 330 to the external server and wirelessly receive the first signal from the external server indicative of a match exists indicating that the single individual is the known individual, and a second wireless communication device configured to wirelessly transmit the second signal to the identification device in response to the first signal.

Technical specialists skilled in the art should understand that, the implementations in this disclosure may be implemented as methods, systems, or computer program products. Therefore, this disclosure may be implemented in forms of a complete hardware implementation, a complete software implementation, and a combination of software and hardware implementation. Further, this disclosure may be embodied as a form of one or more computer program products which are embodied as computer executable program codes in computer writable storage media (including but not limited to disk storage and optical storage).

This disclosure is described in accordance with the methods, devices (systems), and flowcharts and/or block diagrams of computer program products of the implementations, which should be comprehended as each flow and/or block of the flowcharts and/or block diagrams implemented by computer program instructions, and the combinations of flows and/or blocks in the flowcharts and/or block diagrams. The computer program instructions therein may be provided to generic computers, special-purpose computers, embedded computers or other processors of programmable data processing devices to produce a machine, wherein the instructions executed by the computers or the other processors of programmable data processing devices produce an apparatus for implementing the functions designated by one or more flows in the flowcharts and/or one or more blocks in the block diagrams.

The computer program instructions may be also stored in a computer readable storage which is able to boot a computer or other programmable data processing device to a specific work mode, wherein the instructions stored in the computer readable storage produce a manufactured product containing the instruction devices which implements the functions designated by one or more flows in the flowcharts and/or one or more blocks in the block diagrams.

The computer program instructions may also be loaded to a computer or another programmable data processing device to execute a series of operating procedures in the computer or the other programmable data processing device to produce a process implemented by the computer, whereby the computer program instructions executed in the computer or the other programmable data processing device provide the operating procedures for the functions designated by one or more flows in the flowcharts and/or one or more blocks in the block diagrams.

Apparently, the technical specialists skilled in the art may perform any variation and/or modification to this disclosure by the principles and within the scope of this disclosure. Therefore, if the variations and modifications herein are within the scope of the claims and other equivalent techniques herein, this disclosure intends to include the variations and modifications thereof.

What is claimed is:

1. A method for processing biometric measurement data using a computing device, comprising:
receiving at least one biometric measurement record associated with a first biometric measurement generated by contact with a single individual;
extracting, by the computing device and for each of the at least one biometric measurement record, feature data including at least one periodic feature extracted from the at least one biometric measurement record;
determining, by the computing device, pairing data comprising a plurality of candidate pairs between the feature data and defined profiles associated with a known individual, wherein a candidate pair is associated with one of the at least one periodic feature and one of the defined profiles associated with the known individual;

determining, for the candidate pair, a similarity value based on the one of the at least one periodic feature and the one of the defined profiles associated with the known individual; and determining whether a match exists between the single individual and the known individual based on a combination of the similarity values determined for the plurality of candidate pairs.

2. The method of claim 1, wherein the at least one biometric measurement record comprises at least one electrocardiogram (ECG) record.

3. The method of claim 1, wherein the extracting, by the computing device and for each of the at least one biometric measurement record, the feature data including at least one periodic feature extracted from the at least one biometric measurement record further comprises:

removing noises and outliers from each of the at least one biometric measurement record; and extracting a feature data set including the at least one periodic feature from each of the at least one biometric measurement record using at least one technique.

4. The method of claim 3, wherein the plurality of candidate pairs comprises a candidate pair between the feature data set and each of the defined profiles associated with the known individual.

5. The method of claim 3, wherein the at least one biometric measurement record comprises two or more biometric measurement records associated with different biometric modalities, and the feature data set comprises the feature data extracted for each of the two or more biometric measurement records associated with different biometric modalities.

6. The method of claim 5, wherein the two or more biometric measurement records associated with different biometric modalities comprise two or more of an electrocardiograph (ECG) record, a photoplethysmography (PPG) record, and a bioimpedance record.

7. The method of claim 3, wherein the extracting the feature data set including the at least one periodic feature from each of the at least one biometric measurement record using the at least one technique comprises:

extracting a first group of features, as a first part of the feature data set, from the at least one biometric measurement record using a fiducial point based approach, wherein the first group of features comprise at least one of intervals, amplitudes, angles, and other feature data extracted from a delineation of the at least one biometric measurement record; and extracting a second group of features, as a second part of the feature data set, from the at least one biometric measurement record using an appearance based approach, wherein the second group of features comprise at least one of feature data obtained from autocorrelation (AC) of the at least one biometric measurement record, feature data obtained from discrete cosine transform (DCT) of the at least one biometric measurement record, and feature data obtained from linear discriminant analysis (LDA) of the at least one biometric measurement record.

8. The method of claim 1, wherein each of the at least one of the defined profiles associated with the known individual is indicative of a status of the known individual, and the status comprises a movement condition or a health condition.

9. The method of claim 8, wherein the movement condition is one of running, walking, standing, and sitting; and wherein the health condition comprises an indication of the known individual having heart disease based on a Premature Ventricular Contraction (PVC) event or a Premature Atrial Contraction (PAC) event.

10. The method of claim 1, wherein determining, for the candidate pair, a similarity value based on the one of the at least one periodic feature and the one of the defined profiles associated with the known individual comprises:

determining the similarity value, for the candidate pair, based on one or more of: an Euclidean distance, a parameter based on probability, and a parameter based on a first learning technique; and determining a matching result, for the candidate pair, based on the similarity value using a classification technique selected from a threshold technique and a second learning technique.

11. The method of claim 10, wherein the first learning technique comprises a LDA, and the second learning technique comprises a technique based on a support vector machine (SVM) model or a random forest model.

12. The method of claim 10, wherein the threshold technique comprises:

determining, for the candidate pair, whether the similarity value is greater than a predetermined value;

based on a determination that the similarity values is greater than the predetermined value, determining, for the candidate pair, the matching result.

13. The method of claim 1, wherein the determining whether a match exists between the single individual and the known individual based on a combination of the similarity values determined for the plurality of candidate pairs comprises:

determining whether the match exists between the single individual and the known individual using an ensemble learning technique, wherein the ensemble learning technique is selected from a majority voting technique or a third learning technique, and the third learning technique is trained from the feature data associated with the pairing data and the similarities values.

14. The method of claim 1, wherein the feature data associated with the pairing data and the similarities values comprises a distribution of the similarity values.

15. The method of claim 1, further comprising:

receiving at least one biometric measurement record associated with a second biometric measurement generated by contact with the known individual; and extracting, by the computing device and for each of the at least one biometric measurement record associated with the second biometric measurement, one or more of the defined profiles including at least one periodic feature extracted from the at least one biometric measurement record associated with the second biometric measurement.

16. An apparatus for multi-modality biometric identification, comprising:

a non-transitory memory; and a processor configured to execute instructions stored in the non-transitory memory to:

receive at least two biometric measurement signals generated by contact with a single individual, wherein each of the at least two biometric measurement signals is associated with a different biometric modality;

extract, for each of the at least two biometric measurement signals, feature data including at least one periodic feature;

determine pairing data comprising a plurality of candidate pairs between the feature data and defined profiles associated with a known individual, wherein a candidate pair is associated with one of the at least one periodic feature and one of the defined profiles associated with the known individual,
wherein the one of the defined profiles associated with the known individual is indicative of a status of the known individual comprising a movement condition or a health condition;

determine, for the candidate pair, a matching result based on similarity of the one of the at least one periodic feature and one of the defined profiles associated with the known individual; and determine whether a match exists between the single individual and the known individual based on a combination of the matching results determined for the plurality of candidate pairs.

17. The apparatus of claim 16, wherein the two or more biometric measurement records associated with different biometric modalities comprise two or more of: an electrocardiograph (ECG) record, a photoplethysmography (PPG) record, and a bioimpedance record.

18. The apparatus of claim 16, wherein the movement condition is one of running, walking, standing, and sitting; and wherein the health condition comprises an indication of the known individual having heart disease based on a Premature Ventricular Contraction (PVC) event or a Premature Atrial Contraction (PAC) event.

19. An apparatus, comprising:
a body;
at least one biometric sensor coupled to the body to produce a biometric measurement when activated by contact with a single individual;
a non-transitory memory;
a processor configured to execute instructions stored in the non-transitory memory to:

receive at least one biometric measurement record associated with the biometric measurement generated by contact with a single individual;

extract, for each of the at least one biometric measurement record, feature data including at least one periodic feature extracted from the at least one biometric measurement record;

determine pairing data comprising a plurality of candidate pairs between the feature data and defined profiles associated with a known individual, wherein a candidate pair is associated with one of the at least one periodic feature and one of the defined profiles associated with the known individual;

determine, for the candidate pair, a similarity value based on the one of the at least one periodic feature and the one of the defined profiles associated with the known individual; and determine whether a match exists between the single individual and the known individual based on a combination of the similarity values determined for the plurality of candidate pairs; and at least one communication device coupled to the body and controlled by the processor to transmit data, to a reader device, indicating that the single individual is the known individual based on a determination that the match exists.

20. The apparatus of claim 19, wherein the instructions to determine, for the candidate pair, a similarity value based on the one of the at least one periodic feature and the one of the defined profiles associated with the known individual comprise instructions to:
determine the similarity value, for the candidate pair, based on one or more of: an Euclidean distance, a parameter based on probability, and a parameter based on a first learning technique; and
determine a matching result, for the candidate pair, based on the similarity value using a classification technique selected from a threshold technique and a second learning technique.

\* \* \* \* \*